United States Patent [19]

Marion et al.

[11] Patent Number: 5,474,777
[45] Date of Patent: Dec. 12, 1995

[54] TWO-PHASE LIQUID CLEANSING COSMETIC COMPOSITION CONTAINING AT LEAST ONE DIALKYLPHTHALATE AND AN ANIONIC, AMPHOTERIC OR ZWITTERIONIC SURFACE-ACTIVE AGENT

[75] Inventors: Helene Marion, Paris; Nathalie Louvet, L'Hay les Roses; Liliane Lukassen, Chevilly Larue, all of France

[73] Assignee: L'Oreal, Paris, France

[21] Appl. No.: 180,502

[22] Filed: Jan. 12, 1994

Related U.S. Application Data

[63] Continuation of Ser. No. 804,669, Dec. 11, 1991, abandoned.

[30] Foreign Application Priority Data

Dec. 12, 1990 [FR] France .................................. 90 15579

[51] Int. Cl.$^6$ ............................. A61K 7/00; A61K 7/075
[52] U.S. Cl. .................. 424/401; 424/70.21; 424/70.24; 514/938; 514/846; 252/DIG. 5
[58] Field of Search .......................... 424/70, 401, 70.1, 424/70.21, 70.24; 514/937, 938, 846; 252/DIG. 5

[56] References Cited

U.S. PATENT DOCUMENTS

| | | | |
|---|---|---|---|
| 2,528,378 | 10/1950 | Mannheimer | 260/309.6 |
| 2,781,354 | 2/1957 | Mannheimer | 260/309.6 |
| 4,217,344 | 8/1980 | Vanlerberghe et al. | 424/60 |
| 4,732,692 | 3/1988 | Zabotto | 424/59 |
| 4,742,086 | 5/1988 | Masamizu | 521/62 |
| 4,767,741 | 8/1988 | Komor et al. | 512/3 |
| 4,772,471 | 9/1988 | Vanlerberghe et al. | 424/450 |
| 4,781,917 | 11/1988 | Luebbe | 514/740 |
| 4,897,308 | 6/1990 | Vanlerberghe et al. | 428/402.2 |
| 5,021,200 | 6/1991 | Vanlerberghe et al. | 264/4.3 |

FOREIGN PATENT DOCUMENTS 2408387  6/1975  France .

OTHER PUBLICATIONS

Chemical Abstracts, vol. 110, No. 20, May 15, 1989, p. 414, No. 179537v.
Chemical Abstracts, vol. 105, No. 2, Jul. 14, 1986, p. 109, No. 8366f.

Primary Examiner—Gollamudi S. Kishore
Assistant Examiner—Sally Gardner
Attorney, Agent, or Firm—Jacobson, Price, Holman & Stern

[57] ABSTRACT

Liquid cleansing cosmetic composition consisting of an oily phase and an aqueous phase, the oily phase consisting of at least one dialkylphthalate and, optionally, of dialkylphthalate-miscible products, the aqueous phase containing one or more ionic surface-active agents. This two-phase cosmetic composition leaves a feeling of softness on the skin and is provided in an aesthetically attractive form.

6 Claims, No Drawings

TWO-PHASE LIQUID CLEANSING COSMETIC COMPOSITION CONTAINING AT LEAST ONE DIALKYLPHTHALATE AND AN ANIONIC, AMPHOTERIC OR ZWITTERIONIC SURFACE-ACTIVE AGENT

This application is a continuation of application Ser. No. 07/804,669, filed Dec. 11, 1991, now abandoned.

The subject of the present invention is a two-phase liquid cleansing composition containing one or more dialkylphthalates and having an aesthetically attractive appearance.

The Journal of the American College of Toxicology 1985, Vol. 4, pages 267–271, describes the use of a dialkylphthalate as an alcohol denaturant and for retaining perfumes in toilet water and alcohol-containing perfumed lotions.

However, the presence of alcohol is often an irritant and a need exists for an alcohol-free aqueous cosmetic composition.

It has been discovered that the presence of a dialkylphthalate in an aqueous liquid cosmetic composition imparts substantial cosmetic qualities to the composition, in particular, film-forming and softness properties. In effect, dialkylphthalate imparts a feeling of softness to the skin.

It has also been observed that the presence of the dialkylphthalate enhances the durability of the perfume in the composition and on the skin even in the absence of alcohol.

Finally, the use of the dialkylphthalate makes it possible to obtain a two-phase liquid composition exhibiting an aesthetically attractive appearance.

The subject of the invention is an alcohol-free liquid cleansing composition comprising two phases, an aqueous phase and an oily phase. The aqueous phase comprises a surface-active agent. The oily phase comprises 50 to 100% by weight of one or more dialkylphthalates. When the dialkylphthalate content of the oily phase is less than 100% by weight, the complement to 100% consists of one or more dialkylphthalate-miscible products.

As dialkylphthalate-miscible products, there may be mentioned oils, in particular adipates such as dioctyladipate, myristates such as isopropylmyristate, palmitates such as octylpalmitate, stearates such as isopropylstearate, vitamins such as vitamin A, vitamin E and vitamin F, oils such as sunflower oil, fish oil, pentaerythritol 2-tetraethylhexanoate and similar products.

It has been discovered than when the surface-active agent is chosen from anionic, amphoteric or zwitterionic surface-active agents and their mixtures, aesthetically attractive cosmetic compositions in diphasic form are obtained.

The oily phase containing the dialkylphthalate is dispersed on stirring in the form of microbeads in the aqueous phase forming a suspension which, on standing, settles at the bottom of the container producing an aesthetically pleasant powdery effect.

The dialkylphthalates used in the compositions are of the general formula:

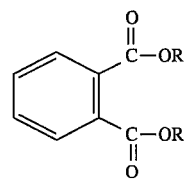

in which R is a $C_1$–$C_4$ alkyl residue, in particular, a methyl, ethyl or butyl residue.

The amount of dialkylphthalate is 0.5 to 20% and preferably 2 to 15% by weight of the total weight of the composition.

The amount of surface-active agent is 0.1 to 30% by weight and preferably 2 to 6% by weight of the total weight of the composition.

The aqueous phase may consist of sterile deionised water or of a floral water such as rose water, bluet water, camomile water or linden water.

The aqueous phase represents 74 to 99.5% and preferably 90 to 95% by weight of the total weight of the composition.

Among the anionic surface-active agents, there may be mentioned more particularly acylisethionates, acylmethyltaurates, alkalimetal salts, magnesium, ammonium, amine or aminoalcohol salts of the following compounds:

alkylsulphates, alkylethersulphates, alkylamidoethersulphates, alkylarylpolyethersulphates, monoglyceridesulphates;

alkylsulphonates, alkylamidesulphonates, alkylarylsulphonates, olefinsulphonates, paraffinsulphonates;

alkylsulphosuccinates, alkylethersulphosuccinates, alkylamidesulphosuccinates;

alkylsulphosuccinamates, alkylsulphoacetates;

alkylphosphates, alkyletherphosphates;

acylsarcosinates;

N-acylpolypeptides.

The alkyl or acyl radical of these various compounds generally consists of a carbon chain comprising 12 to 20 carbon atoms.

Among the anionic surface-active agents, there may also be mentioned:

the salts of fatty acids such as the salts of oleic, ricinoleic, palmitic or stearic acids or of coprah oil or hydrogenated coprah oil acids, and acyllactylates whose acyl radical comprises 8 to 20 carbon atoms.

Among the surface-active agents considered as weakly anionic, there may be mentioned:

the polyoxyalkylene-containing carboxylic ether acids of the formula:

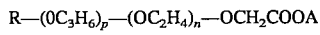

R—(OC$_3$H$_6$)$_p$—(OC$_2$H$_4$)$_n$—OCH$_2$COOA in which R denotes an alkyl radical or a mixture of $C_8$–$C_{22}$, linear or branched, alkyl or alkenyl radicals, a ($C_8$–$C_9$ alkyl)phenyl or a R'CONH—CH$_2$—CH$_2$— radical, with R' denoting a $C_{11}$–$C_{21}$, linear or branched alkyl or alkenyl radical;

n is an integer or a decimal fraction between 2 and 24, p is an integer or a decimal fraction between 0 and 6, A denotes a hydrogen atom or, alternatively, Na, K, Li, ½ Mg or a monoethanolamine, ammonium or triethanolamine residue.

The amphoteric or zwitterionic surface-active agents which are more particularly preferred are:

aliphatic secondary or tertiary amine derivatives in which the aliphatic radical is a linear or branched chain comprising 8 to 18 carbon atoms and which contains at least one water-solubilising carboxylic, sulphonate, sulphate, phosphate or phosphonate anionic group;

($C_8$–$C_{20}$ alkyl)imidazoliniumcarboxymethyls;

($C_8$–$C_{20}$ N-alkyl)-β-iminodipropionates;

($C_8$–$C_{20}$ alkyl)betaines, sulphobetaines, ($C_8$–$C_{20}$ alkyl)amido($C_1$–$C_6$ alkyl)betaines and ($C_8$–$C_{20}$ alkyl)amido($C_1$–$C_6$ alkyl)sulphobetaines.

Among these compounds, there may be mentioned the products sold under the name "MIRANOL" as described in U.S. Pat. Nos. 2,528,378 and 2,781,354 and classified in the CTFA dictionary, 3rd edition, 1982, under the name Amphocarboxyglycinates and Amphocarboxypropionates.

The alkylbetaines are preferably chosen from ($C_{10}$–$C_{20}$ alkyl)betaines.

Due to the presence of the surface-active agent, the compositions are used for example as makeup removers for the face, the presence of dialkylphthalate providing, in this case, a very distinct pleasant feeling, that is to say that no tightness or dryness is felt contrary to what occurs normally when aqueous solutions containing surfactants are used.

According to an embodiment of the invention, the two-phase composition also contains solid particles which are insoluble in the aqueous phase as well as in the oily phase containing the dialkylphthalate, which particles collect at the interface of the beads of the oily phase and the aqueous phase and contribute to increasing the stability of the dispersion of the dialkylphthalate microbeads in the aqueous phase. These solid particles should be small in size. Generally, they are less than 10 μm in size.

The insoluble solid particles are preferably chosen from the group consisting of the following inorganic and organic materials: iron oxide, titanium dioxide, antimony oxide, magnesium oxide, alumina, zinc oxide, zinc peroxide, calcium aluminate, silicic acid, magnesium silicoaluminate, talc, mica, colloidal kaolin, bentonite, zinc laurate, polyvinyl chloride, nacre, carbon black and lanolin.

The composition according to the invention may also contain adjuvants normally used in cosmetics. Depending on their nature, hydrophilic or lipophilic, these adjuvants will be dissolved in the aqueous phase or in the oily phase.

Among these adjuvants, there may be mentioned perfumes, preserving agents, colorants, softening agents such as allantoin; plant extracts; fruit extracts; moisturising agents such as glycerin; hydroxyproline; buffers, humectants such as butylene glycol; oils, vitamins, in particular vitamin B5, vitamin E, sequestrants such as ethylenediaminetetraacetic acid (EDTA), complexion-enhancing agents such as guanosine, UV screens and the like.

To prepare the two-phase composition, the aqueous phase is first prepared by dissolving the water-soluble adjuvants in water. If appropriate, the water-insoluble solid particles are dispersed in this aqueous phase either at low temperature or while heating slightly, and then the oily phase containing the dialkylphthalate and, if appropriate, the dialkylphthalate-miscible products and the lipid-soluble adjuvants (oil, perfume and the like) is poured therein. The mixture is stirred for about one hour to one and a half hour and after being allowed to stand, a separation into two phases is obtained.

The invention will be better understood by means of the non-restrictive examples below.

| MAKEUP REMOVER WITH A POWDERY EFFECT | % by weight |
|---|---|
| EXAMPLE 1 | |
| Dibutylphthalate | 10 |
| Perfume | 0.05 |
| Nacre | 0.01 |
| 1-Hydroxyethyl-2-lauryl-3-carboxymethyl-imidazolinium | 2 |
| 2-Hydroxy-4-methoxybenzophenone-5-sulphonic acid (UV screen) sold under the name UVINUL MS 540 by BASF | 0.05 |
| Ethylenediaminotetraacetic acid (EDTA) | 0.05 |
| Preservative | 0.1 |
| Colorant | 0.1 |
| Water qs | 100 |
| EXAMPLE 2 | |
| Dimethylphthalate | 5 |
| Perfume | 0.5 |
| Glycerin | 3.0 |
| Hydroxyproline | 1 |
| Vitamin B5 | 1 |
| 1-Hydroxyethyl-2-lauryl-3-carboxymethyl-imidazolinium | 4 |
| Guanosine | 0.01 |
| Ethylonediaminetetraacetic acid (EDTA) | 0.05 |
| 2-Hydroxy-4-methoxybenzophenone-5-sulphonic acid (UV screen) | 0.05 |
| Preservative | 0.2 |
| Water qs | 100 |
| EXAMPLE 3 | |
| Diethylphthalate | 4 |
| Perfume | 1 |
| Butylene glycol | 2 |
| Glycerin | 3 |
| Citric acid (buffer) | 2 |
| Fruit extracts | 5 |
| Sodium lauryl ether sulphate | 3 |
| Preservative | 0.3 |
| Water qs | 100 |
| EXAMPLE 4 | |
| Diethylphthalate | 15 |
| Dioctyladipate | 10 |
| Nacre | 0.01 |
| Cocoamphocarboxyglycinate sold under the name MIRANOL C2M by the company MIRANOL | 3.3 |
| Alkylethersulphate sold under the name TEXAPON ASV by the company HENKEL | 2.7 |
| Preservatives | 0.2 |
| Sodium benzoate | 2 |
| 2-Hydroxy-4-methoxybenzophenone-5-sulphonic acid (UV screen) sold under the name UVINUL MS 540 by the company BASF | 0.05 |
| Disodium salt of ethylenediamine-tetraacetic acid (EDTA) | 0.05 |
| Water qs | 100 |

We claim:

1. Two-phase alcohol-free liquid cleansing cosmetic composition comprising an aqueous phase and an oily phase wherein:

(i) the aqueous phase represents 74 to 99.5% by weight of the total weight of the composition and contains 0.2–6% by weight of the total weight of the composition of one or more surface-active agents selected from the group consisting of alkylethersulfates and 1-hydroxyethyl-2-lauryl-3-carboxymethylimidazolinium;

(ii) the oily phase consists of 50 to 100% by weight of one or more dialkylphthalates of general formula:

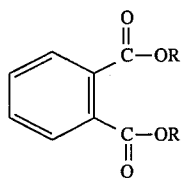

in which R is a $C_1$-$C_4$ alkyl residue;

when the dialkylphthalate content is less than 100% by weight of the oily phase, the complement to 100% consists of one or more dialkylphthalate-miscible products, the one or more dialkylphthalates representing 2 to 15% by weight of the total weight of the composition; and (iii) the oily phase is in the form of microbeads which, on stirring, become suspended in the aqueous phase and, on standing, settle at the bottom of the aqueous phase.

2. Composition according to claim 1, wherein the surface-active agent is sodium lauryl ether sulfate.

3. Composition according to claim 1, wherein
the oily phase consists of 100% by weight of one or more dialkylphthalates.

4. Composition according to claim 1, wherein
the aqueous phase represents 90 to 95% by weight of the total weight of the composition.

5. Composition according to claim 1 also containing at least one adjuvant selected from the group consisting of perfumes, preserving agents, colorants, softening agents, plant extracts, fruit extracts, moisturising agents, buffers, humectants, oils, vitamins, complexion-enhancing agents, UV screens and sequestrants.

6. Composition according to claim 1 also containing solid particles which are insoluble in the aqueous phase and in the oily phase, the said particles being collected at the oil/water interface.

* * * * *